(12) United States Patent
Peters et al.

(10) Patent No.: US 6,808,484 B1
(45) Date of Patent: Oct. 26, 2004

(54) HEART ASSIST DEVICES, SYSTEMS AND METHODS

(75) Inventors: William Suttle Peters, Auckland (NZ); Peter Crispin Lawrence Marsh, Birchgrove (AU); Geoffrey Hamilton White, East Balmain (AU); Rolf Gunnar Unger, Kingsgrove (AU); Frederick Paget Milsom, Auckland (NZ); Hans Hansforth Henrichsen, Shalvey (AU); Colin Edward Sullivan, Birchgrove (AU)

(73) Assignee: Sunshine Heart Company Pty Ltd, New South Wales (AU)

( * ) Notice: Subject to any disclaimer, the term of this patent is extended or adjusted under 35 U.S.C. 154(b) by 334 days.

(21) Appl. No.: 09/869,923

(22) PCT Filed: Jun. 9, 2000

(86) PCT No.: PCT/AU00/00654

§ 371 (c)(1),
(2), (4) Date: Oct. 15, 2001

(87) PCT Pub. No.: WO00/76288

PCT Pub. Date: Dec. 21, 2000

(30) Foreign Application Priority Data

Jun. 10, 1999 (AU) .............................................. PQ0904

(51) Int. Cl.⁷ .............................................. A61N 1/362
(52) U.S. Cl. ....................................................... 600/18
(58) Field of Search ..................................... 600/16–18

(56) References Cited

U.S. PATENT DOCUMENTS

| | | |
|---|---|---|
| 4,014,318 A | 3/1977 | Dockum et al. |
| 4,051,840 A | 10/1977 | Kantrowitz et al. |
| 4,176,411 A | 12/1979 | Runge |
| 4,195,623 A | 4/1980 | Zeff et al. |
| 4,304,225 A | 12/1981 | Freeman |
| 4,457,673 A | 7/1984 | Conley et al. |
| 4,583,523 A | 4/1986 | Kleinke et al. |
| 4,630,597 A | 12/1986 | Kantrowitz et al. |
| 4,697,574 A | 10/1987 | Karcher et al. |
| 4,809,676 A | 3/1989 | Freeman |
| 4,813,952 A | 3/1989 | Khalafalla |
| 4,979,936 A | 12/1990 | Stephenson et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,372,573 A | 12/1994 | Habib |
| 5,429,584 A | 7/1995 | Chiu |
| 5,569,156 A | 10/1996 | Mussivand |
| 5,647,380 A | 7/1997 | Campbell et al. |
| 6,030,336 A | 2/2000 | Franchi |
| 6,045,496 A | 4/2000 | Pacella et al. |
| 6,066,085 A | 5/2000 | Heilman et al. |
| 6,471,633 B1 | 10/2002 | Freed |

FOREIGN PATENT DOCUMENTS

| | | |
|---|---|---|
| EP | 0 216 042 | 4/1987 |
| WO | WO 92/08500 | 5/1992 |
| WO | WO99/04833 | 2/1999 |
| WO | WO 99/04833 | 2/1999 |
| WO | WO01/13974 | 3/2001 |

OTHER PUBLICATIONS

Seymour Furman et al., "Cardiac Support by Periaortic Diastolic Augmentation", New York Journal of Medicine, Aug. 1, 1970, pp. 1964–1969.

J.L. Stewart, "Aortic Cuff a Cardiac Assistance Device", Polytechnic Institute of Brooklyn, 1968, pp. 9–108.

*Primary Examiner*—Scott M. Getzow
(74) *Attorney, Agent, or Firm*—Orrick, Herrington & Sutcliffe LLP

(57) ABSTRACT

An apparatus and method for use in assisting a human heart are disclosed. The apparatus comprises an aortic compression means which may be fully implantable, a fluid reservoir and a pump means adapted to pump a fluid from the reservoir to the aortic compression means so as to actuate the aortic compression means at least partly in counterpulsation with the patient's heart. In addition, the device is adapted to be wholly positioned within the right chest cavity of the patient. The aortic compression means of the device may be curved along its length so as to substantially replicate the curve of the ascending aorta.

49 Claims, 10 Drawing Sheets

HEART ASSIST DEVICES, SYSTEMS AND METHODS

FIELD OF THE INVENTION

The present invention relates to heart assist devices, systems and methods.

BACKGROUND OF THE INVENTION

Currently the only real options for improvement of end-stage heart failure are medical therapy, left ventricular assist devices (LVADS) and transplantation. ACE (Angiotensin Converting Enzyme) inhibitors unload the heart and prolong survival. LVADs pump blood and significantly improve life style and survival, but are complicated to implant, maintain and remove, with relatively high complications relating to bleeding, infection, thromboembolism, and device malfunction.

The transplant rate has stabilised at approximately 2,300 per year in the USA, being limited by organ availability. Transplantation achieves a 75% five year survival rate and a 65% ten year survival rate with significant improvements in functional class.

The number of people awaiting heart transplantation is steadily increasing and they are a sicker group, with increasing numbers requiring hospitalisation, intravenous ionotropes. short-term percutaneous trans-femoral intra-aortic balloon pumping and/or LVAD implantation.

The Institute of Medicine has estimated that by the year 2010, up to 70,000 patients will be candidates for permanent mechanical circulatory support systems.

Over the last ten years, LVADs have been well proven to save lives, acting as bridges to transplantation for critically ill patients. Recently, LVADs have been considered as alternatives to transplantation, and very recently, have been explanted in a few patients who have shown recovery. This latest realisation is starting to gather a lot of interest as researchers focus on recovery of the failing heart. LVADs totally unload the left ventricle and many believe that the heart will then recover. Moreover there is evidence beyond the few patients in whom devices have been removed that there is reversal in markers of heart failure. On the other hand, others have described an increase in myocardial fibrosis which raises a question of whether the heart is being unloaded too much.

The intra-aortic balloon pump (IABP) was first proposed in the 1960s as a method of partial support for the acutely failing heart, for example, after heart surgery or heart attack. It was built as a long thin catheter [10–14 Fr] with an elongated balloon at its tip [volume 30–40 ml]. The balloon was inserted via the femoral artery and inflated and deflated in counterpulsation with the heart beat. Inflation in diastole causes a diastolic pressure augmentation and increases coronary artery blood flow and deflating in systole (triggered by the R wave of the ECG) reduces the afterload, or the pressure head against which the left ventricle has to eject blood. Early investigators determined that the best and most efficient balloon position was closest to the heart, i.e., in the ascending aorta. However, in recent times, the balloon is positioned via the femoral artery in the descending aorta for short term (1–10 days) use. There is substantial proof beyond doubt that counterpulsation works very well in the short-term to assist hearts to recover when drugs (ionotropes etc.) are insufficient or inappropriate to support the cardiovascular system.

Intra-aortic balloon heart pumps operating in counterpulsation assist the heart function. When inflated, the balloon propels blood peripherally from within the aorta to improve blood circulation in the patient. Moreover, more blood is forced into the coronary arteries to help nourish and strengthen the heart muscle. However, the balloon comes into direct contact with the blood flowing into the aorta, which can cause damage to the blood cells and there is a risk of thromboembolism. In addition. current intra-aortic balloon pump systems are inflated by means of a tube passing through the body, the tube connecting the balloon to an external compressor. The opening for the tube to enter the body provides a possible site of infection or other injury. The tube is typically inserted into a groin vessel, the femoral artery, and there is a high risk of associated leg complications. Further, the patient is bedridden and cannot mobilize. Additionally, the use of a gas to inflate the balloon is not an entirely safe operation since any leakage of gas from the balloon into the blood stream could cause an air embolus.

Aortic compression (periaortic diastolic compression) has been described as a means to increase coronary blood flow. For example, U.S. Pat. No. 4,583,523 describes an implantable heart assist device including an elongated assembly extending transversely between the ribs of a patient from the rib cage to the aorta of the heart to be assisted. The assembly includes an aorta compressing device at the front end and a mounting device at the rear end thereof to support the device from the ribs of the patient. A motive device actuates and deactivates the compressing device alternatively to help pump blood through the aorta in a counterpulsation mode of operation. Although this device has advantages for many applications, it does require relatively complicated surgery to implant/explant the device, particularly in regard to the need to mount the device, including its motive means, to the ribs of the patient. Moreover the mounting arrangement and motive means of the device have to be positioned outside the rib cage, making the presence of the device more noticeable to the patient. There is also substantial risk of infection with the device coming through the skin. Furthermore, because the device is attached/mounted to the ribs, there may be shear stresses on the aorta as the rib cage moves with inspiration/expiration. These stresses may cause untoward damage of the aorta.

U.S. Pat. No. 4,979,936 discloses an autologous biologic pump in the form of an apparatus using skeletal muscle formed into a pouch which then surrounds a collapsible. shape-retaining bladder. The bladder is connected to a second bladder enclosed in a sheath around a portion of the aorta. The bladders are filled with a fluid such that when the skeletal muscle contracts in response to an electrical stimulation. the fluid is forced from the first bladder into the second bladder sheathed around the aorta, expanding that second bladder and forcing the aorta to compress. Although this approach may be useful in some circumstances, it is doubtful that it is suitable for long term in that the muscle function would probably degrade over time. Furthermore, the muscle has to be "trained" for many weeks before the device can be relied on to assist blood circulation.

WO 99/04833 discloses a cardiac ventricle aid device which is implanted in the abdominal cavity with an aorta sleeve tube placed on, or inserted in, the descending aorta. A disadvantage of the disclosed device is it has a separate actuator and compliance chamber and its implantation is thus complicated. Another disadvantage is it is difficult to securely mount the device components to a structure in the abdominal cavity that is capable of supporting its weight. A further disadvantage is a number of vertebral arteries stem from the descending aorta which can be damaged during the implantation of the device.

It would be desirable to have a heart assist device that could be quickly and totally implanted in a relatively easy manner and with minimum trauma to the patient and to allow ambulation with low risk of complications. Also desirable would be a heart assist device that allows partial unloading of the heart longterm, augmenting the cardiac output of the native heart, and possibly allowing substantial recovery of the heart so that the device could be weaned. Moreover. it would be desirable for such a device to have no blood contacting surfaces. and not require cardiopulmonary bypass to implant the device. In a small proportion of patients however there will exist aortic disease making a periaortic device unsuitable. In these patients it would be desirable to be able to apply the same aortic counterpulsation, but with a device that replaces the ascending aorta. For this reason reference in this specification to "compression of the aorta" includes compression of a prosthesis replacing a resected portion of the aorta. Such a device would require cardiopulmonary bypass and would be blood contacting, but has the same advantages of allowing partial unloading of the heart longterm, augmenting the cardiac output of the native heart, and possibly allowing substantial recovery of the heart so that the device could be weaned.

It is an object of the present invention to satisfy one or more of the above desirable criteria.

SUMMARY OF THE INVENTION

In a first aspect, the present invention provides a heart assist device adapted for implantation into a patient, the device including
- a) an aortic compression means is so shaped and dimensioned that it is adapted, when actuated, to compress the ascending aorta of a patient;
- b) a fluid reservoir; and
- c) an electrically powered pump means adapted to pump a fluid from the fluid reservoir to the aortic compression means so as to actuate the aortic compression means at least partly in counterpulsation with the patient's heart,
- the fluid reservoir and the pump means are so shaped, dimensioned and interconnected that they are adapted to be wholly positioned within the right chest cavity of the patient.

In a second aspect, the present invention provides a heart assist device adapted for implantation into a patient, the device including:
- a) an aortic compression means which is curved along its length so as to substantially replicate the curve of the ascending aorta adjacent to the aortic compression means and is so shaped and dimensioned that it is adapted, when actuated, to compress the aorta of a patient;
- b a fluid reservoir; and
- c) pump means adapted to pump a fluid from the fluid reservoir to the aortic compression means so as to actuate the aortic compression means at least partly in counterpulsation with the patient's heart,
- the fluid reservoir and the pump means are so shaped, dimensioned and interconnected that they are adapted to be wholly positioned within the chest cavity of the patient.

In a third aspect, the present invention provides a heart assist device adapted for implantation in a patient, the device including:—
- a) an aortic compression means which includes an inflatable cuff and is so shaped and dimensioned that it is adapted to encircle and, when actuated, compress the aorta of a patient, the cuff being substantially C-shaped and including two free ends that are adapted to overlap when the cuff is placed around the aorta;
- b) a fluid reservoir; and
- c) pump means adapted to pump a fluid from the fluid reservoir to the aortic compression means so as to actuate the aortic compression means at least partly in counterpulsation with the patient's heart,
- the fluid reservoir and the pump means are so shaped, dimensioned and interconnected that they are adapted to be wholly positioned within the chest cavity of the patient.

In a fourth aspect, the present invention provides a heart assist device adapted for implantation in a patient, the device including:—
- a) an aortic compression means which includes an inflatable cuff and is so shaped and dimensioned that it is adapted to substantially encircle and, when actuated, compress the aorta of a patient, the cuff having two free ends, one of which includes an elongate tongue adapted for suturing or other connection in an overlapping relationship to the other end to retain the cuff in place around the aorta:
- b) a fluid reservoir; and
- c) pump means adapted to pump a fluid from the fluid reservoir to the aortic compression means so as to actuate the aortic compression means at least partly in counterpulsation with the patient's heart,
- the fluid reservoir and the pump means are so shaped, dimensioned and interconnected that they are adapted to be wholly positioned within the chest cavity of the patient.

In a fifth aspect, the present invention provides a heart assist device adapted for implantation in a patient, the device including:—
- a) an aortic compression means which, when actuated, compress the aorta of a patient;
- b) a fluid reservoir; and
- c) pump means adapted to pump a fluid from the fluid reservoir to the aortic compression means so as to actuate the aortic compression means at least partly in counterpulsation with the patient's heart,
- the fluid reservoir and the pump means are so shaped, dimensioned and interconnected that they are adapted to be wholly positioned within the chest cavity of the patient and the pump means and the fluid reservoir are provided in a fluid filled substantially air-tight housing.

In a sixth aspect, the present invention provides a heart assist device adapted for implantation in a patient, the device including:—
- a) an aortic compression means adapted, when actuated, to compress the ascending aorta of a patient;
- b) a liquid reservoir;
- c) a pump means adapted to pump a liquid from the liquid reservoir to the aortic compression means so as to actuate the compression means, the liquid reservoir and the aortic compression means being adapted to be positioned in close juxtaposition with one another within the chest cavity of the patient, and
- d) means to sense the pressure in the liquid in the absence of aortic compression and alter the sensed pressure to a predetermined pressure In a seventh aspect, the present invention provides an aortic compression means for use in a heart assist device, the aortic compression means including:

a) an elastic inflatable cuff adapted to be placed about the ascending aorta of a patient; and b) a flexible, substantially inelastic, sheath adapted to extend around the cuff and at least assist in retaining it in position on the aorta, wherein the aortic compression means is curved along its length so as to substantially replicate the curve of the ascending aorta adjacent to the aortic compression means.

In a eighth aspect, the present invention provides an aortic compression means for use in a heart assist device, the aortic compression means including:

a) an elastic inflatable cuff adapted to be placed about the ascending aorta of a patient; and b) a flexible, substantially inelastic, sheath adapted to extend around the cuff and at least assist in retaining it in position on the aorta, wherein the cuff is substantially C-shaped and includes two free ends that are adapted to overlap when the cuff is placed around the aorta.

In a ninth aspect, the present invention provides an aortic compression means for use in a heart assist device. the aortic compression means including:

a) an elastic inflatable cuff adapted to be placed about the ascending aorta of a patient; and b) a flexible, substantially inelastic, sheath adapted to extend around the cuff and at least assist in retaining it in position on the aorta, wherein the cuff is substantially C-shaped and includes two free ends, one of the free ends includes an elongated tongue adapted for suturing or otherwise connected in an overlapping relationship to the other end to retain the device adjacent the aorta.

In a tenth aspect, the present invention provides a heart assist device including:

a) an aortic compression means adapted by its shape and dimensions to be placed around the ascending aorta of a patient; and b) an actuation means to periodically actuate the aortic compression means in at least partial counterpulsation with the heart, wherein the aortic compression means and the actuation means are placed wholly within the right chest cavity of the patient.

In an eleventh aspect, the present invention provides a heart assist device adapted for implantation wholly into a bodily cavity of a patient, the device including:

a) an aortic compression means adapted, when actuated, to compress an aorta of a patient;

b) a housing with an exterior surface;

c) a fluid reservoir in the housing, the fluid reservoir having a flexible exterior surface forming part of the housing exterior surface; and d) a pump means adapted to pump a fluid from the fluid reservoir to the aortic compression means so as to actuate the aortic compression means at least partly in counterpulsation with the patient's heart, wherein the fluid reservoir flexible exterior surface is adapted to contract during aortic compression and expand in the absence of aortic compression and is further adapted to be positioned substantially adjacent a flexible organ in the patient's bodily cavity.

Preferably, the bodily cavity is the thoracic cavity and the organ is the lung.

In a further aspect, the present invention provides an implantable system for assisting the functioning of the heart of a subject, the system including:

an implantable device for assisting the functioning of the heart of a subject, including:

means for externally engaging and compressing the aorta;

motive means responsive to control signal(s) for actuating and de-activating the compressing means cyclically to help blood pump through the aorta, wherein the compressing means and the motive means are fully implantable within the thoracic cavity of the subject and wherein the compressing means and/or motive means include means adapted for attachment to the aorta and/or surrounding tissue within the thoracic cavity of the subject;

sensing means adapted for sensing the heart and generating sensing signals;

control means responsive to the sensing signals for generating the control signal(s); and a power source for providing power to the motive means.

The device of the invention may operate in countersynchronisation to the heart (counterpulsation).

An advantage of the device and system of the present invention is that the risk of limb ischemia associated with conventional IAB systems is avoided because there is no blood contact with the device whatsoever. Patient ambulation is also possible. Additionally the implantation technique used for the device of the invention is less invasive than those required for other devices. In particular, compared to the arrangement taught in U.S. Pat. No. 4,583,523, the device of the present invention provides a better outcome in term of reduced risk of infection, cosmesis and ease of implant and explant.

A further advantage of the device and system of the present invention is that there is little risk to the patient in the event of device failure. The device has the great advantage of being able to be weaned and turned off in the event of cardiac recovery. This is simply not possible with known LVADS. Furthermore if the heart shows signs of relapsing back into failure, the device can be switched back on.

The compressing means of the device of the present invention preferably includes a preshaped balloon cuff for wrapping around a portion of the aorta. Preferably, the balloon is configured longitudinally to fit the curve, that of a circular or oval arc, of the ascending aorta. In a particularly preferred form of the device of the present invention, the cross-section of the cuff is C-shaped, allowing wrapping of the cuff with some overlap around the aorta. Preferably, the cuff is shaped such that it does concentrically compress the length of enclosed aorta and spreads the compression forces evenly, reducing any wear or fatigue on any one part of the aorta. The balloon cuff is enclosed within a flexible and non-elastic outer sleeve. The sleeve has an elongated "tongue" on one arm of the C-shaped cuff and this is passed around the aorta to be secured by suturing or other means on the outer aspect of the other arm of the C-shaped cuff. This arrangement stops the balloon inflation force from going outwards. Furthermore, the preshaped cuff and flexible sleeve are particularly designed to create a snug fit and low profile on the aorta, to reduce damage to the aorta and surrounding structures, and to create maximum efficiency of the device.

In a preferred form of the invention, the device is adapted for compression of the ascending aorta. An upper mid-line sternotomy provides easy surgical access to the ascending aorta and has the further advantage of not being very painful for the patient. A minimum incision is required in this procedure. In this mode of use of the device of the invention, the compressing means is preferably adapted to squeeze approximately 15–25 ml of blood from the ascending aorta in each compression cycle.

The cuff has a single inlet/outlet port for the fluid to move to inflate/deflate the balloon. The fluid used is preferably liquid, such as water or saline, as this is noncompressible and less likely to leak compared to gas. Furthermore, using a liquid allows a fully implantable device so that the patient can mobilize easily. The port and connecting tube to the motive means is of sufficient diameter and length to allow rapid emptying and filling of the cuff without generating too high compression pressures. The fluid must move within 0.15 sec for effective counterpulsation action. The compressive force emptying the cuff is the force exerted by the compressed aorta. This approximately 100 mmHg. A tube lumen of approximately 1 to 1.5 cm with a length of 3 to 8 cm allows 17 to 25 ml fluid to pass down a gradient of 100 mmHg in less than 0.15 sec. The compressive force filling the cuff is generated by the motive means, and this pressure gradient is approximately the same ie the motive means generates approximately 200 mmHg to allow the fluid to shift into the cuff in less than 0.15 sec.

The port more preferably has a trumpet-shaped or flanged opening into the cuff to spread the fluid more evenly into the balloon during inflation and to assist more rapid deflation. There may be a diffuser mounted within the lumen of the port to reduce the fluid force on the balloon cuff during inflation.

Preferably, the motive means drives the fluid via a fluid filled sac contained within the motive means. The motive means of the device of the invention may be any means that is capable of cyclically compressing and decompressing the fluid sac. The motive means may be a mechanical or an electromechanical device. The motive means may be an electric motor/cam arrangement. The motive means may include spring mounted arms driven by a pulse of power to hinged solenoids or the like to drive the pressure plates towards each other and thereby compress the aorta. An example of a suitable motive means is an adaptation of the solenoid actuator described in U.S. Pat. No. 4,457,673, the relevant disclosure of which is incorporated herein by reference. The motive means may also be based on that used in the Novacor N1OO Left Ventricular Assist System.

The motive means is preferably enclosed in an air-tight housing. The housing may have a flexible portion that allows for the fluid shift from the motive means—the flexible portion is presented toward the lung tissue and can thus move back and forth. More particularly the motive means is fully implanted within the thoracic cavity and a pressure compliance membrane "interfaces" with the lung surface. Alternatively the housing may be rigid and when the motive means is activated and the fluid sac compressed, a small vacuum is created within the housing. This vacuum has the advantage of increasing the pressure gradient for subsequent emptying of the cuff, to make emptying more rapid. The level of vacuum could be adjusted by accessing a transcutaneous gas reservoir linked to the housing. A final alternative is to have a external gas line from the motive means to allow gas exhaust, eliminating the need for a compliance chamber, but introducing a percutaneous line that has an increased risk of infection.

The motive means may be designed so that in the event of failure, it automatically goes into "off" with the fluid sac filled so that the aorta is not compressed, thus minimising risk to the patient.

The motive means may include or be associated with means for detecting speed and completeness of cuff filling and emptying, and of monitoring the fluid pressure within the connector tube, means for measuring arterial blood pressure or flow. The motive means may also act to record the ECG, having electrodes positioned on the housing or as separate wires attached to body tissues.

The means adapted for attachment to the aorta and/or surrounding tissue of the subject may be any suitable means. For example, the attachment means may be adapted for suturing and/or gluing the compressing means or motive means to the aorta or the surrounding tissue within the chest cavity. The attachment means may be suturing tabs. The attachment means may be apertures allowing ingrowth of tissue and/or surface portions adapted to promote tissue growth into or onto the compressing means and/or the motive means so as to hold the device in position relative to the aorta. For example, the cuff may have a plurality of holes through which the cuff may be sutured to the aorta. The cuff may also have holes or slits to accommodate coronary artery bypass grafts to the ascending aorta. The motive means will sit within the chest cavity, preferably the right thoracic cavity, between the mediastinum and the right lung.

The sensor means may be means detecting a selected physiological event associated with heartbeat. The sensor means may be any means for producing an ECG. Means for detecting the action potentials of the cardiac muscles, for example electrodes, are well known to those skilled in the art and will not be described in detail here.

The control means may be any means capable of providing an output to actuate the motive means in response to signal(s) providing the sensor means.

The control means may provide signals to the motor means to countersynchronise compression of the aorta with the heart beat to provide counterpulsation, for example, aorta compression may commence with aortic valve closure (ventricular diastole), whilst aorta release occurs just prior to contraction/ejection (ventricular systole).

The power means may be an internal and/or external battery, or TET (transcutaneous electronic transfer).

De-activation of the compressing means may be timed to the R wave of the ECG and may be adapted for adjustment either manually or automatically. The dicrotic notch on the arterial pressure wave may provide the signal for actuation of the compressing means.

In yet a further aspect, the present invention provides a method for improving blood circulation in a subject, the method including implanting a device in accordance with the invention fully within the thoracic cavity of a subject, actuating the compressing means periodically in synchrony with the diastole period to compress the aorta; and alternating the period of actuation with periods of deactivation of the compressing means thereby allowing the aorta to return to its uncompressed shape.

The system and device of preferred embodiments of the invention allow relief/recovery from chronic heart failure whilst allowing the subject to move around freely without being constrained by a large external pumping device.

BRIEF DESCRIPTION OF THE DRAWINGS

Preferred embodiments of the invention will now be described, by way of examples only, with reference to the accompanying drawings in which:

FIG. 1b is an enlarged view of the device shown in FIG. 1a;

FIG. 2a is an enlarged perspective detailed view of the device shown in FIG. 1a;

FIG. 2b is a partial top view of the device shown in FIG. 1a;

FIG. 5b is a perspective view of the device shown in FIG. 5a;

DETAILED DESCRIPTION OF THE PREFERRED EMBODIMENTS

Figure 1A:
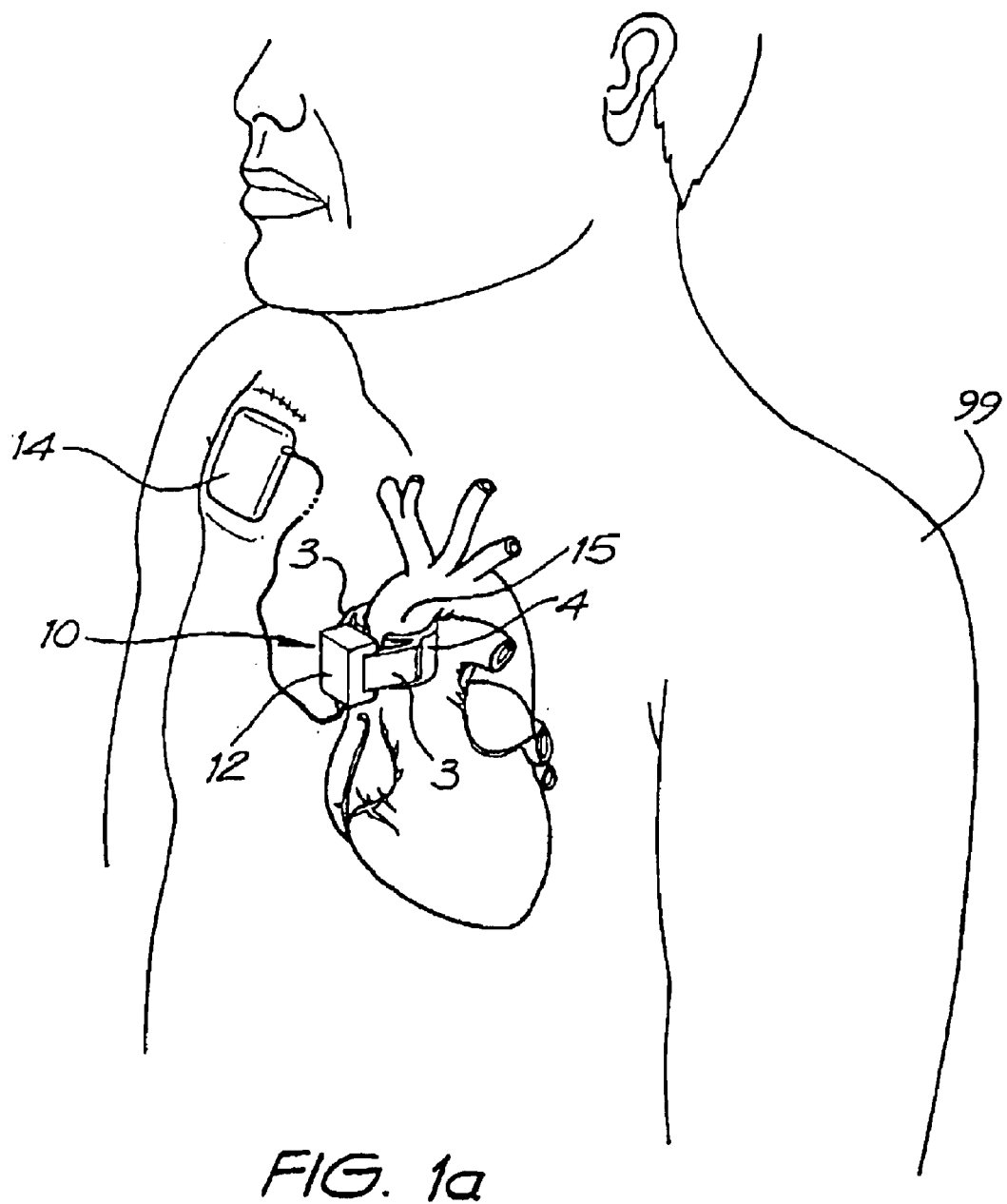
FIG. 1a is a schematic drawing of a first embodiment of a heart assist device according to the invention implanted in the thoracic cavity of a subject.
Figure 1B:
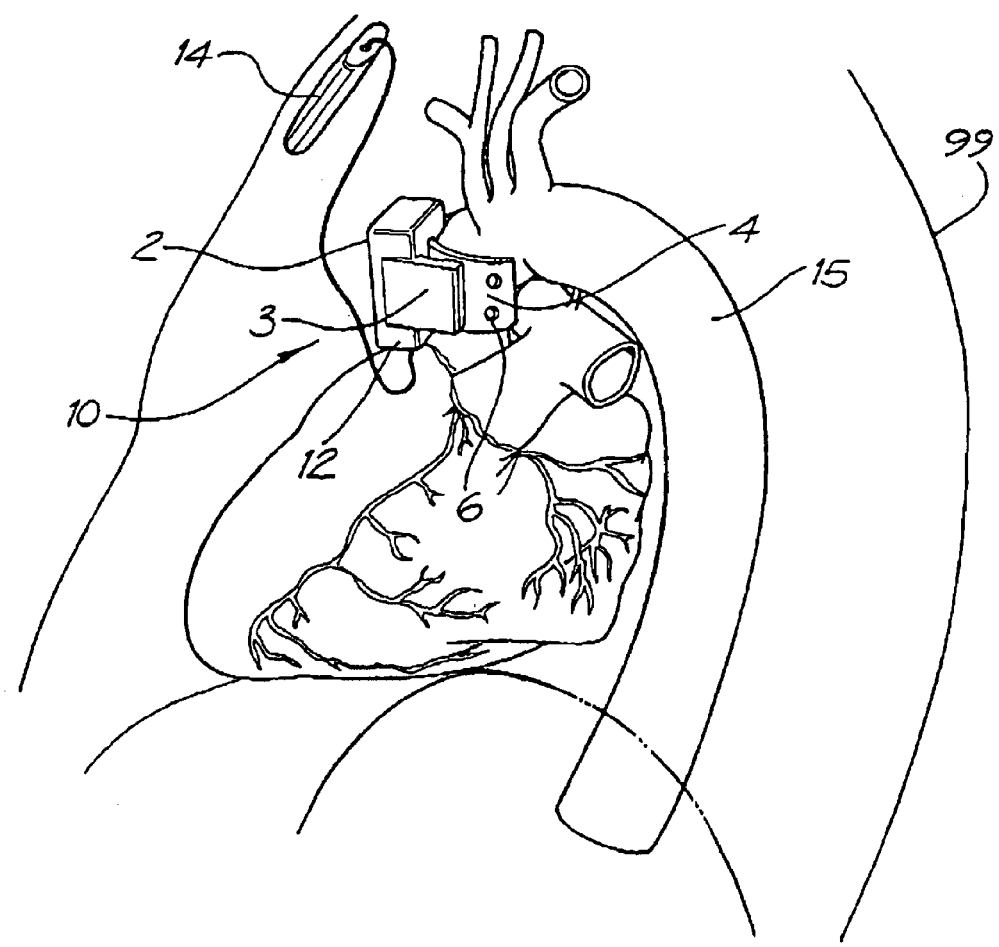

FIGS. 1a to 2b are schematic drawings showing a first embodiment of a heart assist device 10 in accordance with the invention. The device 10 is suitable for complete implantation in the thoracic cavity of a subject 99 adjacent the ascending portion of the aorta 151, as shown. The device 10 includes an aortic compression means in the form of a hinged solenoid 2 (see FIGS. 2a and 2b) in a housing 12. The solenoid 2 is driven by pulses of electrical power from a controller/battery 14 to actuate wedge-shaped compression plates 4 via arms 3. The wedge-shaped plates 4 surround the ascending portion of the aorta 15. When the plates 4 are actuated they approach each other and that part of the aorta 15 between the plates 4 is compressed. The plates 4 have a plurality of holes 6 that provide means for suturing the plates to the aorta 15 and permitting ingrowth of tissue therethrough.

Figure 2A:
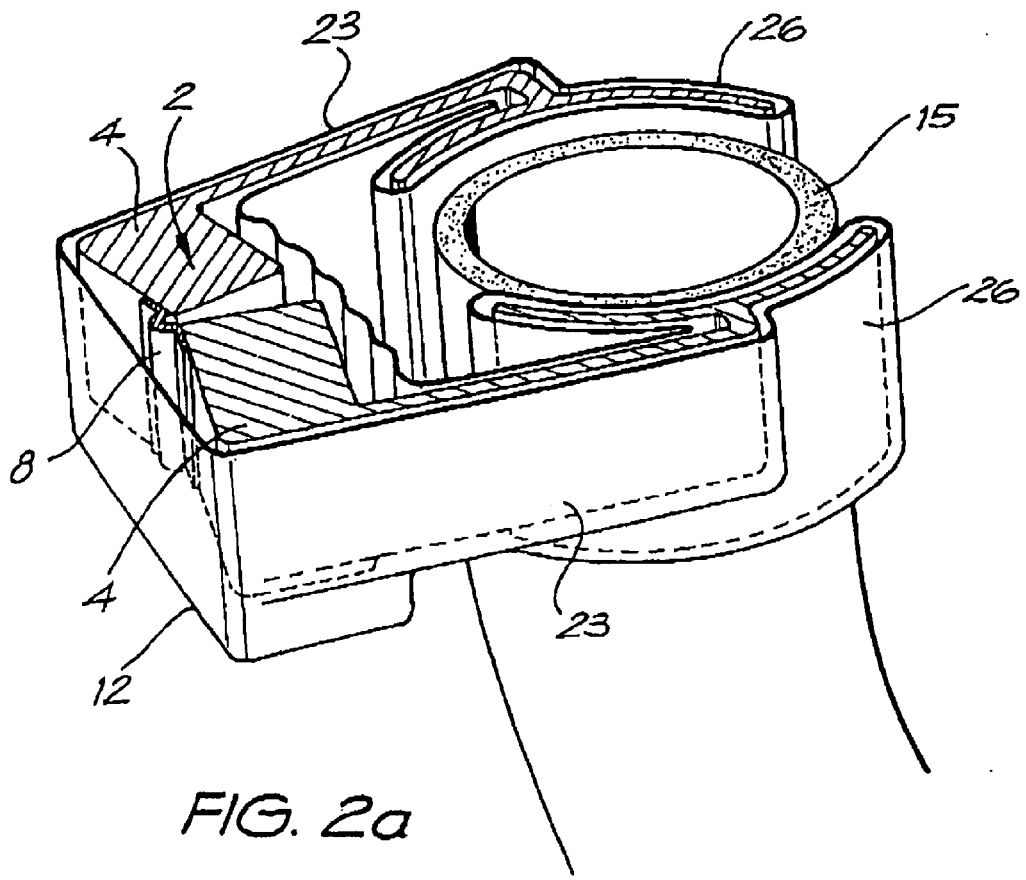
Figure 2B:
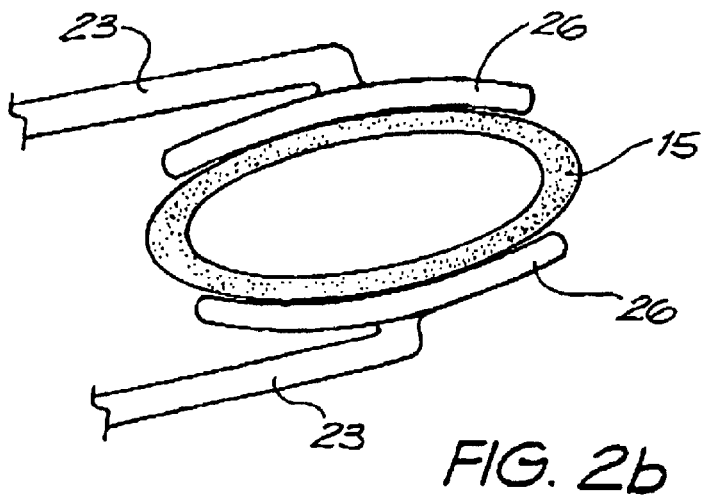

FIGS. 2a and 2b are detailed schematic drawings of the solenoid 2 which show that it includes two arcuate plates 26 hinged at 8. The plates 26 are shown in the deactivated (resting) position in FIG. 2a and are shown in the actuated position in FIG. 2b compressing the aorta 15. The plates 26 are soft form moulded and are actuated by the hinged solenoid 4 via arms 23.

FIGS. 3 to 5b are schematic drawings of second to fourth embodiments of heart assist devices in accordance with the present invention.

Figure 3:
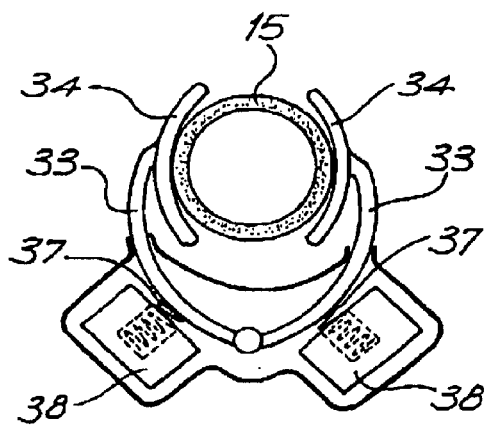
FIG. 3 is top view of a second embodiment of a heart assist device according to the invention.

In the second embodiment shown in FIG. 3, the compression plates 34 are actuated via arms 33, with each of the arms 33 being acted on by a respective rod solenoid 38 acting through springs 37 between the rod solenoid 38 and the respective arm 33.

Figure 4:
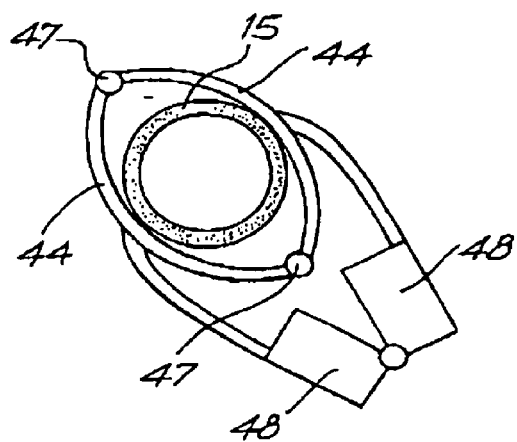
FIG. 4 is a top view of a third embodiment of a heart assist device according to the invention.

In the third embodiment shown in FIG. 4, solenoids 48 act on deformable nitinol plates 44 connected together at either end 47 to encircle the aorta 15.

Figure 5A:
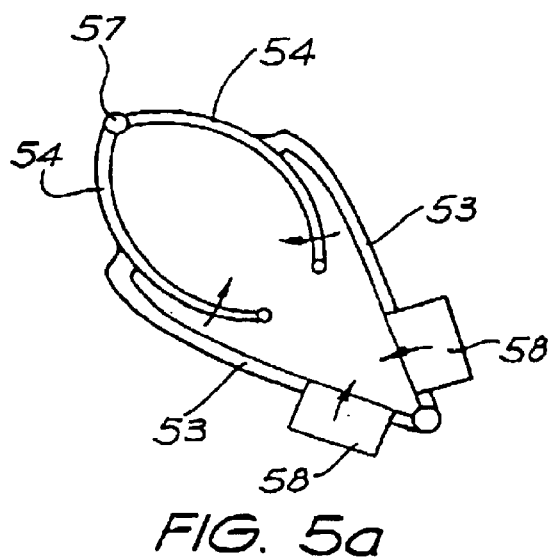
FIG. 5a is a top view of a fourth embodiment of a heart assist device according to the invention.
Figure 5B:
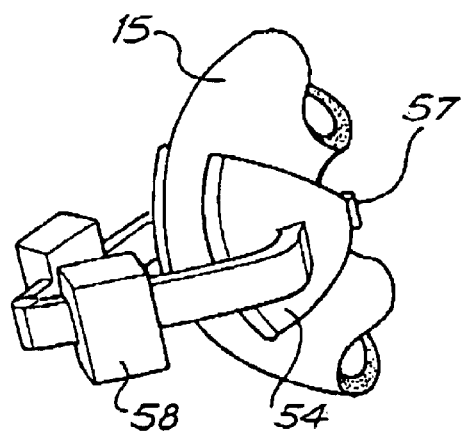

In the fourth embodiment shown in FIGS. 5a and 5b, wedge-shaped plates 54 are connected together at one end 57 and each plate is actuated by solenoids 58 acting through arms 53. As best shown in FIG. 5b, the wedge-shaped plates 54 effectively conform to the shape of the ascending aorta 15.

Figure 6:
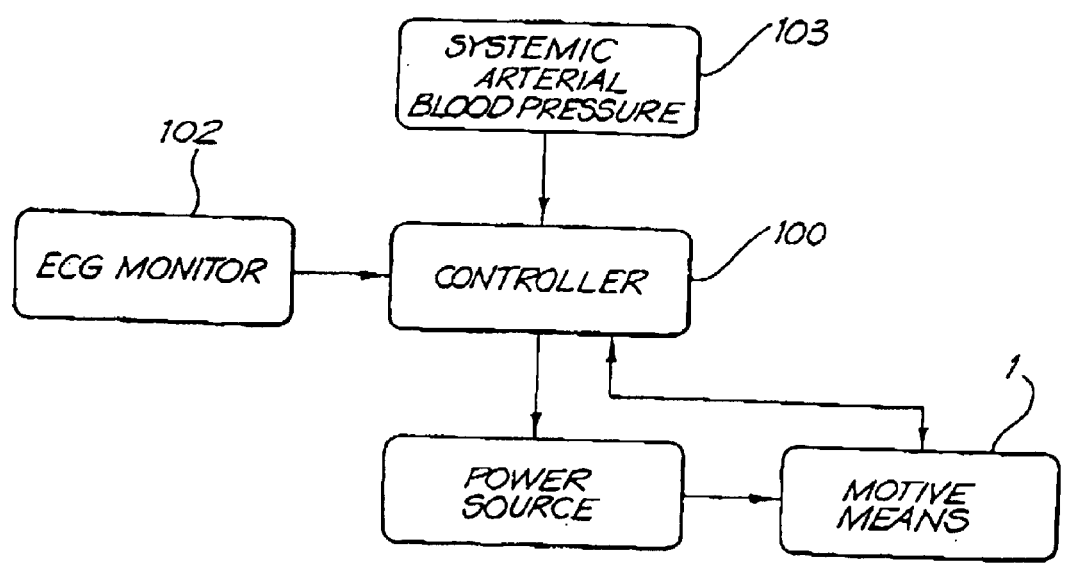
FIG. 6 is a block diagram of an embodiment of a cardiac assist system according to the invention.
Figure 7:
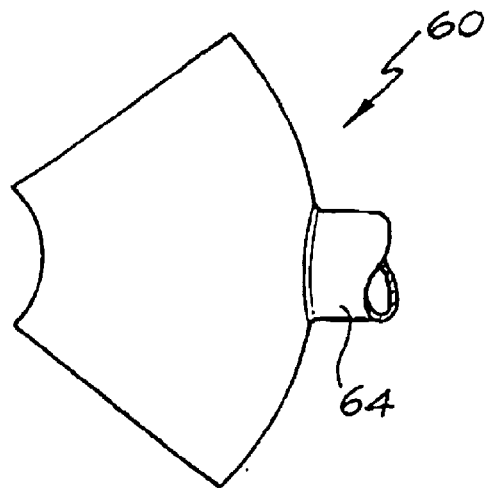
FIG. 7 is a side view of an embodiment of an inflatable cuff.
Figure 8:
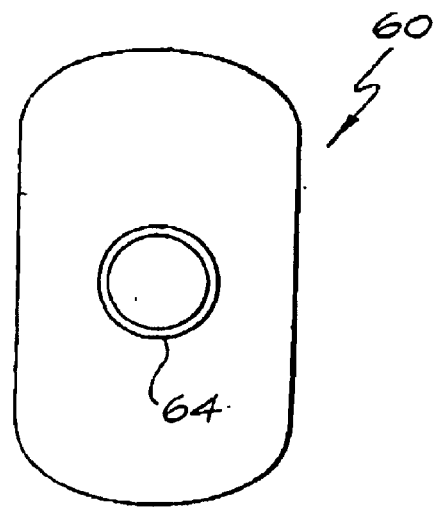
FIG. 8 is a rear view of the cuff shown in FIG. 7.

FIG. 6 is a block diagram of an embodiment of a cardiac assist system constructed in accordance with the invention suitable for use with, for example, the cardiac assist device 10.

Initiation of the compression of the aorta 15 by the compression plates 4 is accomplished by energisation of the solenoid 2. This energisation is under the control of a control means 100 which activates the solenoid 2 of the motive means 1 in response to signals received from an ECG monitor 102 or systemic arterial blood pressure 103 or the like. The ECG monitor 102 and/or the control means 1 are preferably implanted but may be on the body of the subject 99.

In operation, de-activation of the compression plates 4 draws them apart and effectively unloads the left ventricle by allowing the aorta 15 to return to its usual circular shape. The expansion of the aorta 15 between the de-activated plates causes a pressure drop in the aorta 15, facilitating left ventricle ejection (ie unloading of the heart). After the heart has finished ejecting blood into the aorta 15 and the aortic valve closes, the plates 4 are activated to move them towards each other and compress the aorta 15 and thereby squeeze blood out of the volume of the aorta 15 compressed by the compression plates 4 and augment the diastolic pressure. Coronary artery blood flow to the left ventricle occurs predominantly in diastole so compression of the aorta 15 also augments coronary blood flow.

Figure 9A:
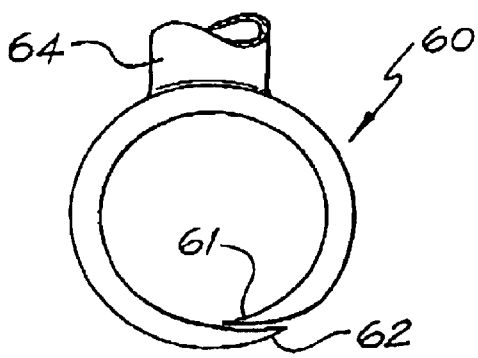
FIG. 9a is a top view of the cuff shown in FIG. 7.
Figure 9B:
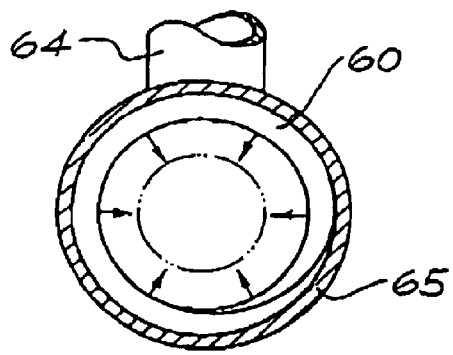
FIG. 9b is a top view of the cuff shown in FIG. 7 after application of an external sheath.
Figure 10:
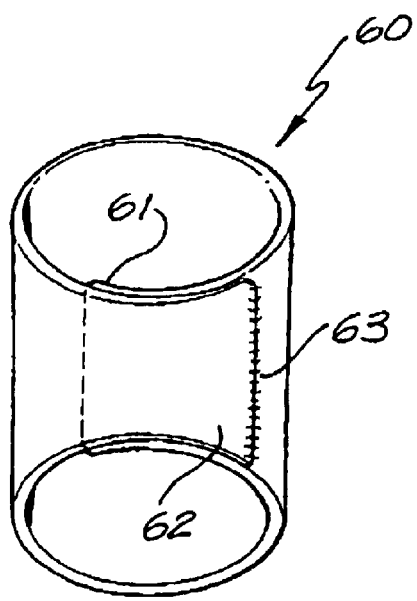
FIG. 10 is a front view of the cuff shown in FIG. 7.

FIGS. 7 to 10 show an aortic compression means in the form of a flexible hollow inflatable cuff 60. The cuff 60 is curved along its length so as to substantially replicate the curve of the aorta 15 adjacent thereto. The cuff 60 is shown in its de-activated (uninflated) state in FIG. 9a, and has two free ends 61 and 62 which are adapted to overlap when the cuff 60 is placed around the aorta. As best shown in FIG. 10, the cuff 60 is retained adjacent the aorta after implantation by suturing the two free ends together at 63. This also ensures that the cuff 60 is a snug fit around the aorta, when the aorta is in its usual circular shape.

Further, as best shown in FIG. 9b. a substantially inelastic, flexible sheath 65 is also preferably placed around the cuff 60. The sheath 65 assists in retaining the cuff 60 adjacent the aorta and inwardly concentrates the compression forces generated by inflation of the cuff 60, as indicated by arrows 66. The sheath 65 can also have free ends sutured together to retain it and the cuff 60 adjacent the aorta in addition to, or in place of, the cuff sutures 63. The sheath 65 is preferably made from DACRON (Trade Mark), KEVLAR (Trade Mark), TEFLON (Trade Mark), GORE--TEX (Trade Mark), polyurethane or other flexible inelastic biocompatible materials. The sheath 65 is preferably glued, fused or otherwise bonded to the cuff 60.

The cuff 60 also has a single inlet/outlet port 64 for the introduction of fluid to inflate the cuff 60 and thereby compress the aorta and the removal of fluid for the deflation of the cuff and relaxing of the aorta. The fluid is preferably water or an isotonic solution of salt or other low-viscosity, non-toxic liquid.

The fluid is actively pumped into the cuff 60 for inflation into the shape indicated in phantom in FIG. 9b. The cuff 60 can be actively deflated by suctioning the fluid from the cuff 60. Alternatively, the cuff 60 can be passively deflated by the blood pressure of the constricted aorta re-expanding and returning the cuff 60 to the state shown in FIG. 9a, which ejects the fluid from the cuff 60. It is preferable to actively deflate the cuff 60 as it gives better presystolic unloading of the heart and counteracts any high intrathoracic pressures, such as when the subject coughs. In either case, the natural resilience of the cuff 60 also assists in deflation by biasing the cuff 60 to the shape shown in FIG. 9b.

In another embodiment of heart assist device (not shown), the compression plates 4 are used to squeeze the cuff 60. This embodiment can be configured to operate in two ways. Firstly, the plates 4 can provide a larger aortic compression and the cuff 60 a smaller aortic compression, either simultaneously or one after the other. This reduces the fluid requirements of the cuff 60. Secondly, the cuff 60 can be set at a fixed inflation and provide a cushion between the plates 4 and the aorta.

In other embodiments of cuff (not shown), the sheath is integrally formed with the cuff, preferably by moulding, or in the form of flexible, inelastic fibres embedded in the cuff.

FIGS. 11 to 18 are schematic drawings of fifth to tenth embodiments of heart assist devices in accordance with the present invention that utilise the cuff 60 shown in FIGS. 7 to 10.

Figure 11:
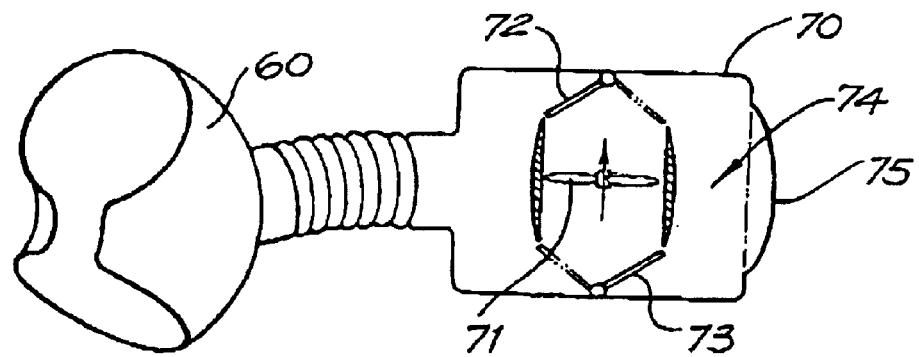
FIG. 11 is a fifth embodiment of a heart assist device according to the invention.

In the fifth embodiment shown in FIG. 11, the cuff 60 is closely coupled to a fluid-filled air-tight housing 70 that has therein a pump, in the form of rotatable impeller 71 and a pair of valves 72 and 73 for directing the flow of the impeller 71. The housing also includes an inlet/outlet 76 in fluid communication with the inlet/outlet port 64 of the cuff 60. A fluid reservoir is also provided in the housing 70 in the form of an internal portion 74 of the volume of the housing 70, as is a pressure compliance means, in the form of a substantially flexible portion of 75 of the housing 70.

In operation, energisation of the impeller 71 with the valves 72 and 73 in the position shown in FIG. 11 causes fluid to be actively withdrawn from the cuff 60, which allow the aorta to return to its usual circular shape. This fluid is pumped into the internal portion 74 of the housing 70 and causes the flexible portion 75 to expand to the position shown in FIG. 11. When the valves 71 and 73 are in the positions shown in phantom in FIG. 11 and the impeller 71 is energised, the fluid in the portion 74 is pumped into the cuff 60 to expand same and to compress the aorta. The removal of fluid from the portion 74 causes the flexible portion 75 to retract to the position shown in the phantom in FIG. 11. As with earlier embodiments, the control of the impeller and valves is in response to signals received from an ECG monitor or systemic arterial blood pressure or the like.

Figure 12:
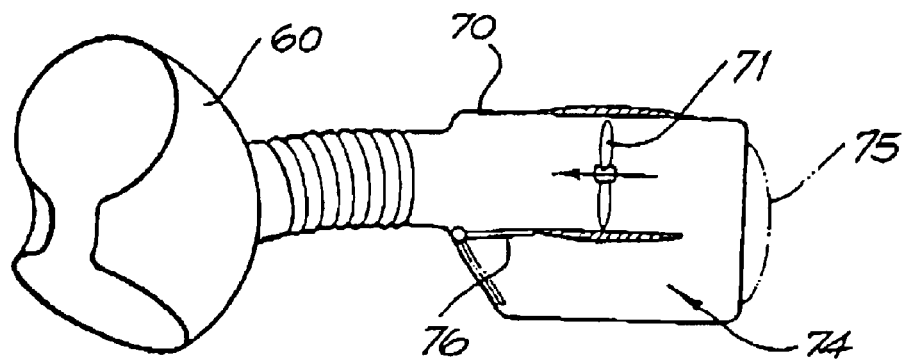
FIG. 12 is a schematic side view of a sixth embodiment of a heart assist device according to the invention.

In the sixth embodiment shown in FIG. 12. the device has only a single valve 76. The aorta is compressed by positioning the valve 76 as shown in FIG. 12 and energising the impeller 71. When the valve 76 is moved to the position shown in phantom in FIG. 2 and impeller is de-energised the expanding aorta passively ejects the fluid back into the portion 74 of the housing 71 and causes the flexible portion 75 to expand to the position shown in phantom.

Figure 13:
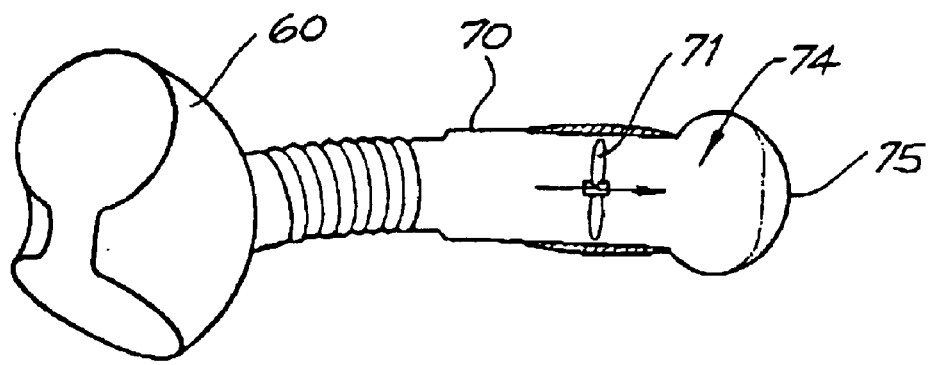
FIG. 13 is a schematic side view of a seventh embodiment of a heart assist device according to the invention.
Figure 14:
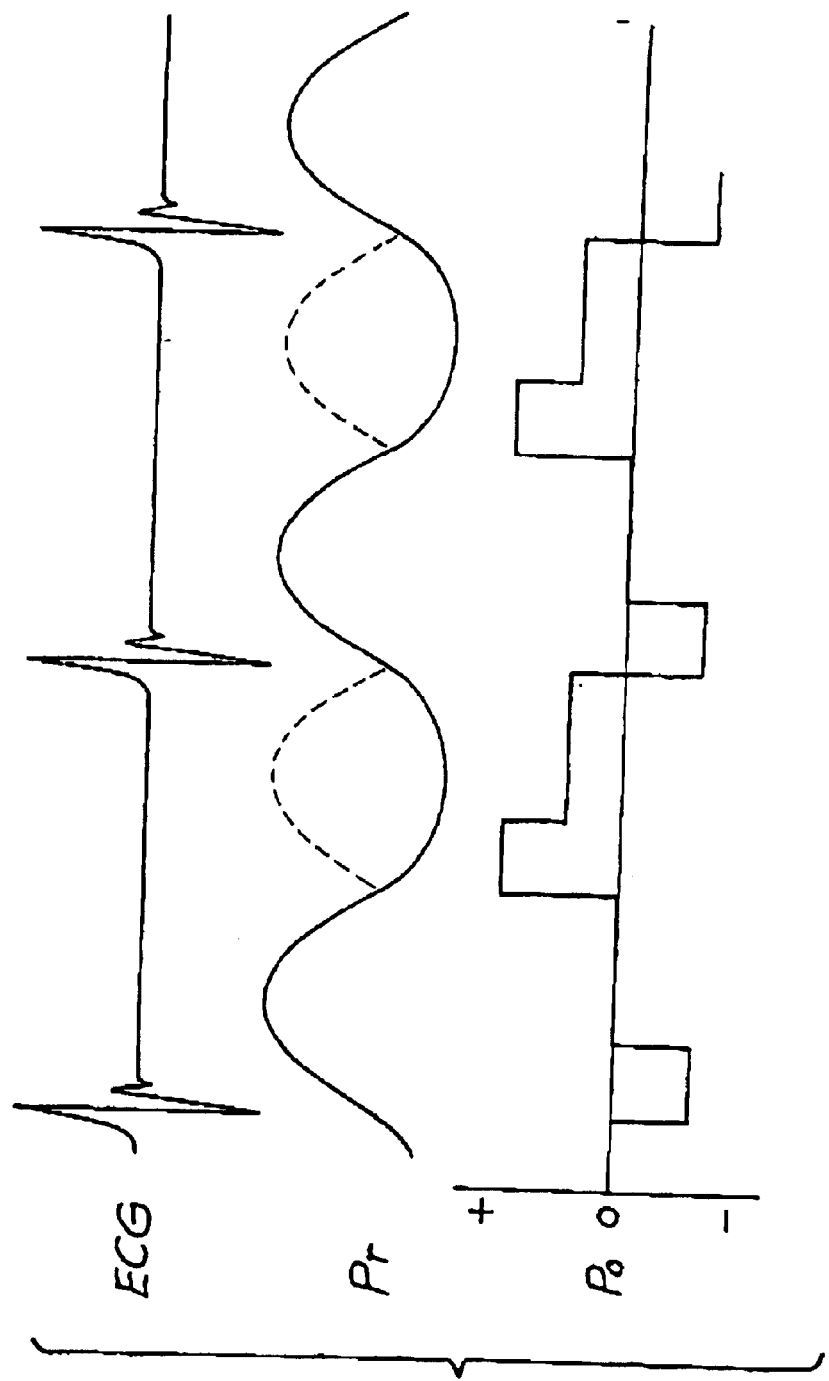
FIG. 14 is an indication of an electrical cardiograph (ECG) readout, heart diastolic pressure (Pr.) and power supply (Po) for the device shown in FIG. 13.

In the seventh embodiment shown in FIG. 13, the impeller 71 is driven in one direction to cause fluid flow in the direction indicated by the arrow to deflate the cuff 60 and expand the flexible portion 75. Reversing the direction of the impeller 71 causes the flexible portion 75 to retract to the position shown in phantom as fluid is displaced into the cuff 60 to inflate same. This embodiment requires variable power control to the motor driving the impeller 71 and a plot of the motor power requirements (Po) relative to the subject's electro cardiograph reading (ECG) and aortic pressure (Pr.) are shown in FIG. 14.

Figure 15:
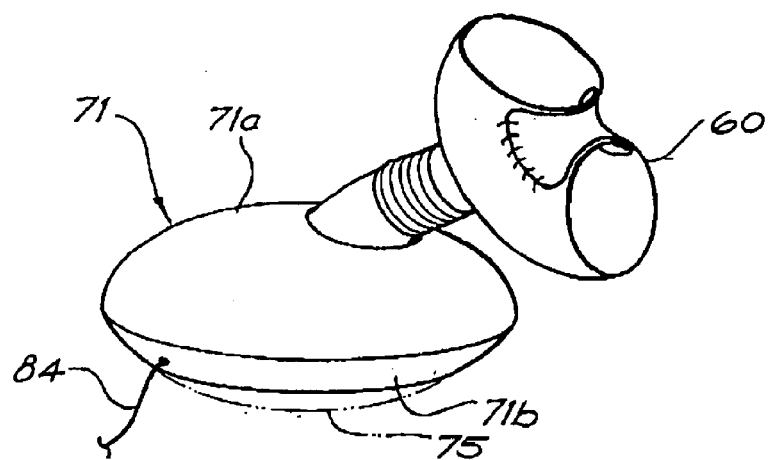
FIG. 15 is a schematic side view of an eighth embodiment of a heart assist device according to the invention.
Figure 16:
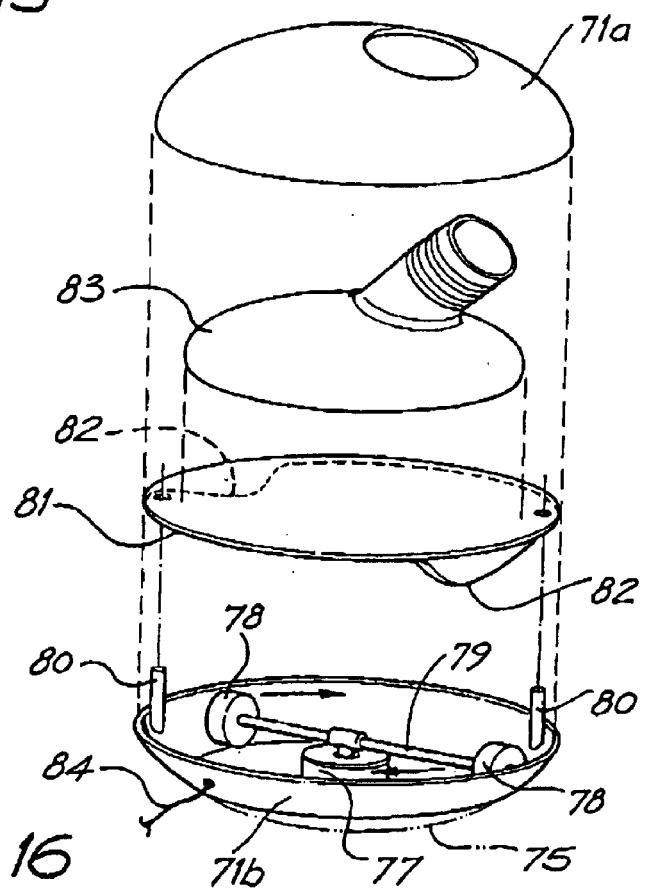
FIG. 16 is an exploded view of the pump housing of the device shown in FIG. 15.

In the eighth embodiment shown in FIGS. 15 and 16, the housing 71 has a rigid upper portion 71a and a partially rigid lower portion 71b that includes the flexible portion 75. A motor 77 is mounted in the lower portion 71b that drives a pair of rollers 78, each positioned on an end of a common shaft 79. The housing portion 71b also has a pair of upstanding guide posts 80 which are slidably received in corresponding holes in a swash plate 81. The swash plate 81 has a pair of cam formations 82 on its underside. A fluid-filled sac 83 is positioned between the swash plate 81 and the housing portion 71a. The interior of the sac 83 is in fluid communication with the interior of the cuff 60. Power is supplied to the motor 77 through line 84.

In operation, the motor 77 is energised to rotate the rollers 78, which ride along the cam formations 82 to drive the swash plate 81 upwards to compress the sac 83 and eject the fluid therein into the cuff 60 to inflate same. When the rollers 78 have passed the cams 82 the swash plate 81 returns to its original position and the expanding aorta passively ejects the fluid back into the sac 83. In an alternative embodiment (not shown), the rollers 78 are linked to the cam formations 82 to drive the swash plate 81 up and down and thereby actively inflate and actively deflate the cuff 60. As a further alternative, (not shown) a stepper motor(s) can be used to drive the swash plate.

Figure 17:
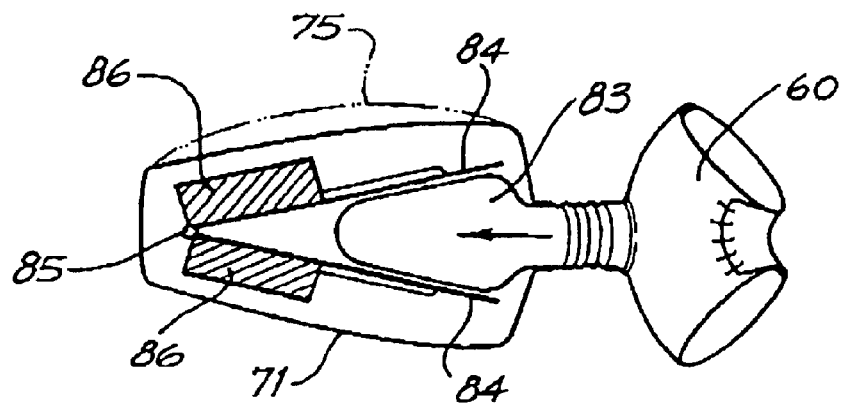
FIG. 17 is a schematic cross sectional view of a ninth embodiment of a heart assist device according to the invention.

In the ninth embodiment shown in FIG. 17, the housing 71 has a fluid filled sac 83 positioned between a pair of compression plates 84 which are hinged at 85 and driven by a solenoid 86. Energising the solenoid 86 brings the plates 84 together to squeeze the sac 83 and force the liquid therein into the cuff 60 to inflate same. De-energising the solenoid 86 draws the plates 84 apart and the expanding aorta passively ejects the fluid back into the sac 83. As with earlier embodiments, as the sac 83 inflates the flexible portion 75 of the housing 71 expands to accommodate the increase in pressure in the housing 71.

Figure 18:
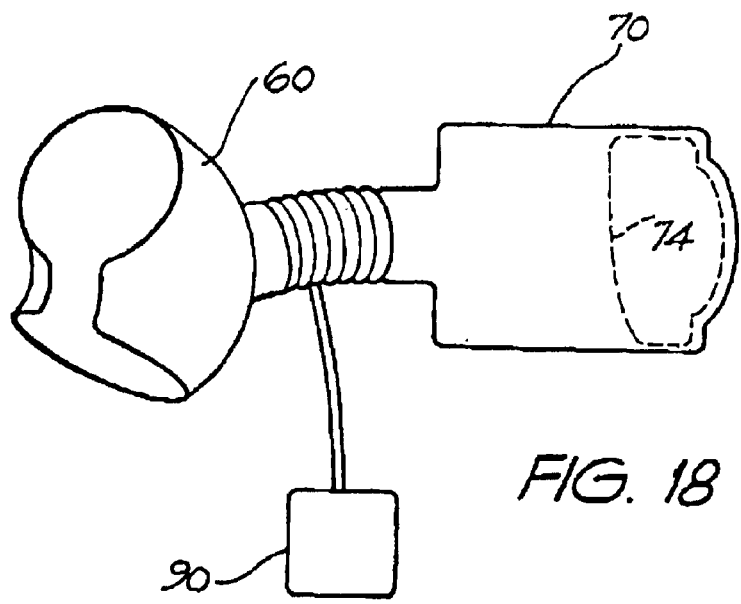
FIG. 18 is a schematic view of a tenth embodiment of a heart assist device according to the invention.

In the tenth embodiment shown in FIG. 18, the heart assist device includes a liquid pressure adjustment means, in the form of remote reservoir 90, connected between the cuff 60 and the reservoir 74. Liquid can be added to the heart assist device, via the remote reservoir 90, to adjust the liquid retained in the (de-activated) cuff 60 and thereby adjust the pressure therein. This allows the size of the cuff 60 to be adjusted to compensate for changes in the size of the aorta and/or the amount of aortic compression to be adjusted to, for example, wean the patient from the heart assist device. When the reservoir is positioned near the skin, its volume can be adjusted by using a needle to inject or withdraw liquid. When the reservoir is positioned near the heart assist device, its volume can be adjusted by adding or withdrawing liquid via a transcutaneous tube. The pressure in the reservoir 90 can also be sensed and automatically adjusted so as to maintain a predetermined pressure.

It will be appreciated that the system and device of the present invention, in their preferred forms, are designed to be simple with no blood contact and a much lower morbidity risk compared to LVADS. The device and system allows the heart to remain totally un-instrumented, and the device, by effective counterpulsation in the aorta, augments the cardiac output up to 15–20%. All natural blood pathways are maintained. Pulsatile blood flow is also maintained. The patient is able to ambulate and there is no risk of leg ischaemia.

The present invention provides for long term relief and/or stabilization/ of or recovery from chronic heart failure. Moreover the present invention may be a suitable bridging device for transplantation.

The device and system of the above-described embodiments improve cardiac work efficiency by reducing the afterload (pressure/resistance to flow which the heart has to overcome to eject blood) during systole (ejection phase), by augmenting diastolic aortic blood pressure to maintain a greater mean arterial pressure, and by increasing left ventricular coronary artery blood flow during diastole.

The preferred embodiments of the heart assist device compress the ascending aorta. This is advantageous as the ascending aorta is less prone to disease than the descending aorta and, being closer to the heart, provides improved pumping efficiency and thus a smaller heart assist device.

It will be appreciated by persons skilled in the art that numerous variations and/or modifications may be made to the invention as shown in the specific embodiments without departing from the spirit or scope of the invention as broadly described. For example, although the invention has been described in specific reference to compression of the aorta, the devices, systems and methods of the present invention can equally be used for the compression of the pulmonary artery to effectively act as a right ventrical assist device, and the present invention extends to this alternative aspect. The present embodiments are, therefore, to be considered in all respects as illustrative and not restrictive.

What is claimed is:

1. A heart assist device adapted for implantation into a patient, the device including:
   a) an aortic compression means which is curved along its length so as to substantially replicate the curve of the ascending aorta adjacent to the aortic compression means and is so shaped and dimensioned that it is adapted, when actuated, to compress the aorta of a patient;
   b) a fluid reservoir; and
   c) pump means adapted to pump a fluid from the fluid reservoir to the aortic compression means so as to actuate the aortic compression means at least partly in counterpulsation with the patient's heart,
   the fluid reservoir and the pump means are so shaped, dimensioned and interconnected that they are adapted to be wholly positioned within the chest cavity of the patient.

2. A device as claimed in claim 1, further including a liquid conduit between the liquid reservoir and the aortic compression device which has a minimum cross sectional area of at least 1 sq cm.

3. A device as claimed in claim 1, wherein the pump means is adapted for active compression of the aortic compression means and active decompression of the aortic compression means.

4. A device as claimed in claim 1, wherein the pump means is adapted for active compression of the aortic compression means and passive decompression of the aortic compression means.

5. A device as claimed in claim 1, further including a liquid pressure adjustment means between the aortic compression means and the liquid reservoir and in fluid communication with the aortic compression means and the liquid reservoir.

6. A device as claimed in claim 5, wherein the liquid pressure adjustment means is a remote reservoir positioned near the patient's skin that is adapted for the receiving or the removal of liquid therein via a needle though the skin.

7. A device as claimed in claim 6, wherein the liquid pressure adjustment means is a remote reservoir positioned in the chest cavity that is adapted for the receiving or the removal of liquid therein via a transcutaneous tube connected thereto.

8. A device as claimed in claim 1, further including a means to sense the pressure in the liquid pressure adjustment means in the absence of aortic compression and alter the sensed pressure to a predetermined pressure.

9. A heart assist device adapted for implantation into a patient, the device including:
   a) an aortic compression means which includes an inflatable cuff and is so shaped and dimensioned that it is adapted to encircle and, when actuated, compress the aorta of a patient, the cuff being substantially C-shaped and including two free ends that are adapted to overlap when the cuff is placed around the aorta;
   b) a fluid reservoir; and
   c) pump means adapted to pump a fluid from the fluid reservoir to the aortic compression means so as to actuate the aortic compression means at least partly in counterpulsation with the patient's heart,
   the fluid reservoir and the pump means are so shaped, dimensioned and interconnected that they are adapted to be wholly positioned within the chest cavity of the patient.

10. A heart assist device adapted for implantation into a patient, the device including:
    a) an aortic compression means which includes an inflatable cuff and is so shaped and dimensioned that it is adapted to substantially encircle and, when actuated, compress the aorta of a patient, the cuff having two free ends, one of which includes an elongate tongue adapted for suturing or other connection in an overlapping relationship to the other end to retain the cuff in place around the aorta;
    b) a fluid reservoir; and
    c) pump means adapted to pump a fluid from the fluid reservoir to the aortic compression means so as to actuate the aortic compression means at least partly in counterpulsation with the patient's heart,
    the fluid reservoir and the pump means are so shaped, dimensioned and interconnected that they are adapted to be wholly positioned within the chest cavity of the patient.

11. A heart assist device adapted for implantation into a patient, the device including:
    a) an aortic compression means which, when actuated, compress the aorta of a patient;
    b) a fluid reservoir; and c) pump means adapted to pump a fluid from the fluid reservoir to the aortic compression means so as to actuate the aortic compression means at least partly in counterpulsation with the patient's heart, the fluid reservoir and the pump means are so shaped, dimensioned and interconnected that they are adapted to be wholly positioned within the chest cavity of the patient and the pump means and the fluid reservoir are provided in a fluid filled substantially air-tight housing.

12. An aortic compression means for use in a heart assist device, the aortic compression means including:
   a) an elastic inflatable cuff adapted to be placed about the ascending aorta of a patient; and
   b) a flexible, substantially inelastic, sheath adapted to extend around the cuff and at least assist in retaining it iii position on the aorta,
   wherein the aortic compression means is curved along its length so as to substantially replicate the curve of the ascending aorta adjacent to the aortic compression means.

13. A device as claimed in claim 12, wherein the cuff is adapted to at least partially encircle the aorta.

14. A device as claimed in claim 13, wherein the cuff is adapted to completely encircle the aorta of the patient.

15. A device as claimed in claim 12 wherein the cuff is substantially C-shaped and includes two free ends that are adapted to overlap when the cuff is placed around the aorta.

16. A device as claimed in claim 12 wherein one of the free ends includes an elongated tongue adapted for suturing in an overlapping relationship to the other end to retain the device adjacent the aorta.

17. A device as claimed in claim 12 wherein the cuff is a snug fit around the aorta of the patient.

18. A means as claimed in claim 12, wherein the sheath is a snug fit around the cuff.

19. A device as claimed in claim 12, wherein the cuff has a single inlet/outlet port.

20. A device as claimed in claim 19, wherein the sheath has an opening complimentary to the cuff inlet/outlet port.

21. A device as claimed in claim 12, wherein the cuff is inflatable to an enlarged pressurised configuration to compressing the aorta and relaxes to a static configuration to relax the aorta.

22. An aortic compression device as claimed in claim 12 when placed in a human or other animal.

23. An aortic compression means for use in a heart assist device, the aortic compression means including:
   a) an elastic inflatable cuff adapted to be placed about the ascending aorta of a patient; and
   b) a flexible, substantially inelastic, sheath adapted to extend around the cuff and at least assist in retaining it in position on the aorta,
   wherein the cuff is substantially C-shaped and includes two free ends that are adapted to overlap when the cuff is placed around the aorta.

24. An aortic compression means for use in a heart assist device, the aortic compression means including:
   a) an elastic inflatable cuff adapted to be placed about the ascending aorta of a patient; and
   b) a flexible, substantially inelastic, sheath adapted to extend around the cuff and at least assist in retaining it in position on the aorta,
   wherein the cuff is substantially C-shaped and includes two free ends, one of the free ends includes an elongated tongue adapted for suturing or otherwise connected in an overlapping relationship to the other end to retain the device adjacent the aorta.

25. A heart assist device adapted for implantation wholly into a bodily cavity of a patient, the device including;
   a) an aortic compression means adapted, when actuated, to compress an aorta of a patient;
   b) a housing with an exterior surface;
   c) a fluid reservoir in the housing, the fluid reservoir having a flexible exterior surface forming part of the housing exterior surface; and
   d) a pump means adapted to pump a fluid from the fluid reservoir to the aortic compression means so as to actuate the aortic compression means at least partly in counterpulsation with the patient's heart,
   wherein the fluid reservoir flexible exterior surface is adapted to contract during aortic compression and expand in the absence of aortic compression and is further adapted to be positioned substantially adjacent an organ in the patient's chest cavity.

26. A device as claimed in claim 25, wherein the bodily cavity is the thoracic cavity and the organ is the lung.

27. A heart assist device adapted for implantation into a patient, the device including:
   a) an aortic compression means is so shaped and dimensioned that it is adapted, when actuated, to compress the ascending aorta of a patient;
   b) a fluid reservoir;
   c) an electrically powered pump means adapted to pump a fluid from the fluid reservoir to the aortic compression means so as to actuate the aortic compression means at least partly in counterpulsation with the patient's heart,
   the fluid reservoir and the pump means are so shaped, dimensioned and interconnected that they are adapted to be wholly positioned within the right chest cavity of the patient; and
   wherein the aortic compression means is curved along its length so as to substantially replicate the curve of the aorta adjacent to the aortic compression means.

28. A heart assist device as claimed in claim 27 when placed in a human or other animal.

29. A heart assist device adapted for implantation into a patient, the device including:
   a) an aortic compression means is so shaped and dimensioned that it is adapted, when actuated, to compress the ascending aorta of a patient;
   b) a fluid reservoir;
   c) an electrically powered pump means adapted to pump a fluid from the fluid reservoir to the aortic compression means so as to actuate the aortic compression means at least partly in counterpulsation with the patient's heart,
   the fluid reservoir and the pump means are so shaped, dimensioned and interconnected that they are adapted to be wholly positioned within the right chest cavity of the patient;
   wherein the aortic compression means includes an elastic inflatable cuff adapted to at least partly encircle the aorta; and
   wherein the cuff is substantially C-shaped and includes two knee ends that are adapted to overlap when the cuff is placed around the aorta.

30. A device as claimed in claim 29 wherein one of the free ends includes an elongated tongue adapted for suturing in an overlapping relationship to the other end to retain the device adjacent the aorta.

31. A heart assist device adapted for implantation into a patient, the device including:
a) an aortic compression means is so shaped and dimensioned that it is adapted, when actuated, to compress the ascending aorta of a patient;
b) a fluid reservoir;
c) an electrically powered pump means adapted to pump a fluid from the fluid reservoir to the aortic compression means so as to actuate the aortic compression means at least partly in counterpulsation with the patient's heart,
the fluid reservoir and the pump means are so shaped, dimensioned and interconnected that they are adapted to be wholly positioned within the right chest cavity of the patient, wherein the pump means and the fluid reservoir are provided in a fluid-filled substantially air-tight housing.

32. A device as claimed in claim 31, further including a pressure compliance means.

33. A device as claimed in claim 32, wherein the pressure compliance means forms part of the housing.

34. A device as claimed in claim 33, wherein the pressure compliance means is a substantially rigid portion of the housing downstream of the pump means, the portion being of sufficient rigidity so as to not deform inwardly during aortic compression nor deform outwardly in the absence of aortic compression.

35. A device as claimed in claim 33, wherein the pressure compliance means is a substantially flexible portion of the housing downstream of the pump means, the portion being of sufficient flexibility so as to deform inwardly during aortic compression and deform outwardly in the absence of aortic compression.

36. A device as claimed in claim 35, wherein the flexible portion is adapted to be positioned in juxtaposition with a lung of the patient and deform outwardly to slightly compress the lung in the absence of aortic compression.

37. A device as claimed in claim 36, wherein the cuff has a single inlet/outlet port.

38. A device as claimed in claim 37, wherein the port has a diffuser therein.

39. A device as claimed in claim 37, wherein the housing has an inlet/outlet port opening in fluid communication with the cuff inlet/outlet port.

40. A device as claimed in claim 31 wherein the aortic compression means is curved along its length so as to substantially replicate the curve of the aorta adjacent to the aortic compression means.

41. A heart assist device adapted for implantation into a patient, the device including:
a) an aortic compression means adapted, when actuated, to compress the ascending aorta of a patient;
b) a liquid reservoir;
c) a pump means adapted to pump a liquid from the liquid reservoir to the aortic compression means so as to actuate the compression means, the liquid reservoir and the aortic compression means being adapted to be positioned in close juxtaposition with one another within the chest cavity of the patient wherein the distance between the liquid reservoir and the aortic compression means is no more than 6 cm., and
d) means to sense the pressure in the liquid in the absence of aortic compression and alter the sensed pressure to a predetermined pressure.

42. A heart assist device adapted for implantation into a patient, the device including:
a) an aortic compression means adapted, when actuated, to compress the ascending aorta of a patient;
b) a liquid reservoir;
c) a pump means adapted to pump a liquid from the liquid reservoir to the aortic compression means so as to actuate the compression means, the liquid reservoir and the aortic compression means being adapted to be positioned in close juxtaposition with one another within the chest cavity of the patient wherein the distance between the liquid reservoir and the aortic compression means is no more than 6 cm.,
d) means to sense the pressure in the liquid in the absence of aortic compression and alter the sensed pressure to a predetermined pressure, and
e) a pressure compliance means, and wherein the liquid reservoir, the pump means and the pressure compliance means are provided in an air-tight housing.

43. A device as claimed in claim 42, wherein the housing is fluid-filled and the liquid reservoir is a portion of the interior of the housing.

44. A device as claimed in claim 42, wherein the pressure compliance means is a flexible portion of the housing adjacent the liquid reservoir.

45. A device as claimed in claim 44, wherein the flexible portion is adapted for positioning in juxtaposition with the lung of the patient.

46. A heart assist device including:
a) an aortic compression means adapted by its shape and dimensions to be placed around the ascending aorta of a patient; and
b) mechanical or electrical actuation means to periodically actuate the aortic compression means in at least partial counterpulsation with the heart,
wherein the aortic compression means and the actuation means are placed wholly within the right chest cavity of the patient,
wherein the aortic compression means is inflatable to compress the aorta and the actuation means includes a fluid reservoir, a pressure compensation means and a pump means adapted to pump fluid into the aortic compression means to inflate same and wherein the pump means, fluid reservoir and pressure compensation means are contained a fluid-filled air-tight housing.

47. A device as claimed in claim 46, wherein the pump means is an impeller adapted to drive fluid from the fluid reservoir and the aortic compression means.

48. A device as claimed in claim 46, wherein the pump means is a fluid-filled sac adapted to be compressed to drive fluid from the sac to the aortic compression means.

49. A device as claimed in claim 46, wherein the aortic compression means is an inflatable cuff adapted for positioning about the aorta of the patient.

* * * * *